(12) United States Patent
Harada et al.

(10) Patent No.: US 7,758,879 B2
(45) Date of Patent: Jul. 20, 2010

(54) DEVICE FOR DISPENSING INSECTICIDE/REPELLENT

(75) Inventors: Tetsuo Harada, Ibaraki (JP); Tomonori Iwasaki, Sanda (JP)

(73) Assignee: Sumitomo Chemical Company, Limited, Osaka (JP)

(*) Notice: Subject to any disclaimer, the term of this patent is extended or adjusted under 35 U.S.C. 154(b) by 1165 days.

(21) Appl. No.: 10/831,206

(22) Filed: Apr. 26, 2004

(65) Prior Publication Data

US 2004/0228896 A1 Nov. 18, 2004

(30) Foreign Application Priority Data

May 12, 2003 (JP) ............................ P 2003-132675

(51) Int. Cl.
*A01N 25/34* (2006.01)
(52) U.S. Cl. .................. 424/409; 424/133; 424/134; 424/136; 424/139; 424/141; 206/215; 206/447; 220/23.82; 220/528; 428/34.2; 428/53; 514/919
(58) Field of Classification Search .................. 43/133, 43/134, 136, 139, 141; 206/215, 447; 220/23.83, 220/23.88, 23.91, 528; 424/409; 428/34.2, 428/53; 514/919
See application file for complete search history.

(56) References Cited

U.S. PATENT DOCUMENTS 3,826,036 A 7/1974 Neugebauer
3,858,807 A * 1/1975 Rabussier et al. ............. 239/56
6,327,813 B1 12/2001 Ishiwatari

FOREIGN PATENT DOCUMENTS

| DE | 196 11 993 | 4/1997 |
|---|---|---|
| EP | 0 100 730 | 2/1984 |
| ES | 369390 | 5/1971 |
| ES | 376205 | 3/1972 |
| GB | 270470 | 5/1927 |
| GB | 1 298 906 | 12/1972 |
| JP | 11-322504 | 11/1999 |
| JP | 2000-189032 | 7/2000 |
| JP | 2000-197438 | 7/2000 |
| JP | 2001-114615 | 4/2001 |
| JP | 2002-153197 | 5/2002 |

* cited by examiner

*Primary Examiner*—Neil Levy
(74) *Attorney, Agent, or Firm*—Wenderoth, Lind & Ponack, L.L.P.

(57) ABSTRACT

The device for dispensing a volatile insecticide or repellent includes a sheet impregnated with an insecticidal/repellent component which volatilizes at an ordinary temperature; a flat box for detachably holding the sheet, the flat box having a sheet-exposing aperture for volatilizing the insecticidal component from the held impregnated sheet; and a suspension cord for three-dimensionally assembling a plurality of the flat box.

2 Claims, 14 Drawing Sheets

(a)

(b)

(d) (e)

(c)

(a)

(b)

(a)

(b)

(d) (e)

(c)

(a)

(b)

DEVICE FOR DISPENSING INSECTICIDE/REPELLENT

BACKGROUND OF THE INVENTION

The present invention relates to a device for dispensing a volatile insecticide or repellent (hereinafter referred to as insect killer) having a sheet impregnated with an insecticidal component which volatilizes at an ordinary temperature.

A conventional insect killer widely used comprises a mat impregnated with a solution of an insecticidal component and a heating device for holding the mat and heating it by a heater, wherein the insecticidal component is vaporized and diffused into the atmosphere. In such an insect killer, the active component-volatilizing time is generally about 8 hours per one mat. Such an insect killer is a most popular one.

For the purpose of vaporizing the insecticide and diffusing it into the atmosphere, the above heating-type insect killer essentially has a heater-equipped heating device for heating the mat impregnated with the insecticide solution. Thus, such an insect killer has the problem that it cannot be used without an outlet for supplying power to the heater.

On the other hand, some ordinary temperature-volatilizing agents are known, which can diffuse an insecticidal component without heating. However, the ordinary temperature-volatilizing agents capable of diffusing the non-heated insecticidal component can provide a low diffusion efficiency depending on the type of the insecticidal component, because the vaporized insecticide can stay around the insecticide source in a saturated state so that additional diffusion of the insecticide can be inhibited.

As disclosed in Patent Literature 1 listed below, such an ordinary temperature-volatilizing agent is often applied to an insect repellent, for example, which is housed in a container comprising male and female parts 101 and 102 (as shown in FIGS. 13(a) and 13(b)) bonded together and which is placed for use in a relatively narrow space such as a chest and a closet.

The applicant has previously proposed an insect killer in Patent Literature 2 or 3 listed below.

Referring to FIG. 14, Patent Literature 2 discloses an insect killer 200 including: insecticide carriers 201 of paper impregnated with an insecticidal component which volatilizes at an ordinary temperature; and a spiral spring 202 as a power source, wherein the insecticide carriers 201 are driven and rotated by the restoring force of the spiral spring 202.

In such a structure, the insecticide carriers 201 are driven and rotated so that the saturated state of the insecticidal component can be avoided and that the diffusion of the insecticidal component can be facilitated near the surface of each insecticide carrier 201. Thus, the insecticide-diffusion efficiency can be increased so that the insect killer can be used in a relatively wide space such as a living room. Additionally, the structure using the spiral spring as a power source needs no external energy supply source such as an electric outlet.

Patent Literature 1: Japanese Patent Application Laid-Open (JP-A) No. 2002-153197 published on May 28, 2002

Patent Literature 2: JP-A No. 2000-197438 published on Jul. 18, 2000

Patent Literature 3: JP-A No. 2001-114615 published on Apr. 24, 2001

SUMMARY OF THE INVENTION

It is generally preferable that the insect killer as mentioned above can have a compact storage form when it is on the market or not used during the off-season. In terms of the efficiency of volatilization of the active component, it is preferable that the insecticide carrier 201 impregnated with the insecticidal component which volatilizes at an ordinary temperature extends as widely as possible.

In conclusion, it is preferable that the insect killer can easily be assembled or converted from a compact form into a working form in which the insecticide carrier extends widely.

The present invention has been made to solve the above problems. It is therefore an object of the invention to provide an insect killer which can have a slim and compact form during commercial sale or storage, can easily be assembled for use and can have a high efficiency of diffusion of the insecticidal component so that it can exert its effect in a relatively wide space such as a living room.

In completing the invention, the inventors have made active investigations to provide an insect killer structure which can be stored in a compact form and can be assembled into a working form in which a wide area is established for the diffusion of the insecticidal component so as to provide an increased efficiency of diffusion of the insecticidal component.

Thus, the present invention is directed to an insect killer, comprising: a sheet impregnated with an insecticidal component which volatilizes at an ordinary temperature; a flat holder for detachably holding the sheet, the flat holder having a sheet-exposing aperture for volatilizing the insecticidal component from the held sheet; and a support member for three-dimensionally assembling a plurality of the flat holders.

According to the invention, the sheet is detachably held in the flat holder, and sheets each impregnated with the insecticidal component which volatilizes at an ordinary temperature can be held in a plurality of the flat holders, respectively, which can three-dimensionally be assembled with or on the support member.

The flat holder has the sheet-exposing aperture for volatilizing the insecticidal component from the held sheet. Thus, the insect killer having the three-dimensionally assembled flat holders can be placed in a room to kill a pest such as a mosquito.

The insecticidal component is impregnated in the sheet so that a wide area can be provided for volatilization of the insecticidal component. A plurality of the sheets can provide a further increased efficiency of diffusion of the insecticidal component.

The sheet impregnated with the insecticidal component which volatilizes at an ordinary temperature is held in the flat holder. Thus, the sheet can be prevented from being directly touched during use, and such a structure is hygienic. In addition, the flat holder can reinforce the sheet.

Thus, the insect killer provided according to the invention can have a slim and compact form during commercial sale or storage, can easily be assembled for use and can have a high efficiency of diffusion of the insecticidal component so that it can exert its effect in a relatively wide space such as a living room.

In the insect killer of the present invention, the support member may comprise a flexible linear member for three-dimensionally suspending a plurality of the flat holders.

According to the invention, for example, the plurality of the flat holders may be suspended from the ceiling of a room or the like by the flexible linear member, which forms the support member.

Thus, the insect killer of the present invention can easily be set at an airy place so that the efficiency of diffusion of the insecticidal component can further be increased.

In the insect killer of the present invention, the support member may comprise a core member for being placed at a center between the plurality of the flat holders and for radially arranging the flat holders in an upright position.

In the above insect killer, the flat holders may be radially provided in an upright position around the core member, which serves as the support member.

For example, when the insect killer is suspended, it can rotate about the core member by wind blowing so that the efficiency of diffusion of the insecticidal component can further be increased.

In the insect killer of the present invention, the core member may have a hole, and the flat holder may have a side face provided with a pin, which can be inserted into the hole of the core member to allow the flat holder to be attached to the core member.

According to the invention, the pin formed on the side face of the flat holder is inserted into the hole of the core member, so that the insect killer can easily be assembled, which comprises the flat holders radially attached to the core member.

Thus, the insect killer provided according to the invention can have a slim and compact form during commercial sale or storage, can easily be assembled for use with reliability and can have a high efficiency of diffusion of the insecticidal component so that it can exert its effect in a relatively wide space such as a living room.

In the insect killer of the present invention, the flat holder may have a single piece of the pin, and the flat holder may be attached so as to be rotatable about the pin.

In such a structure according to the invention, the flat holder is rotatable about the single pin, so that the angle of the flat holder attached to the core member is easily changeable. For example, therefore, in a suspended insect killer comprising the flat holders radially attached in an upright position, the attachment angle of each flat holder can be changed so that the rotational speed of the insect killer can be controlled to some extent and therefore the efficiency of diffusion of the insecticidal component can be regulated.

In the insect killer of the present invention, the core member may be drivable and rotatable.

In such a structure according to the invention, the core member is drivable and rotatable so that the flat holders radially attached to the core member can be rotated by its driving force about the core member, which serves as a rotating shaft. Thus, the efficiency of diffusion of the insecticidal component can be increased without wind blowing.

In the insect killer of the present invention, the sheet may have a plurality of holes.

In such a structure according to the invention, the holes of the sheet can be effective at securing ventilation, so that the efficiency of diffusion of the insecticidal component can further be increased.

In the insect killer of the present invention, the flat holder may be a flat box having an end portion provided with a sheet-receiving opening for receiving the sheet.

In such a structure according to the invention, the sheet-receiving opening is formed at an end portion of the flat box as the flat holder, and the insecticidal component-impregnated sheet can be inserted from the sheet-receiving opening into the flat box.

In such a structure, the insecticidal component-impregnated sheet can easily be replaced. Thus, the sheet running out of the insecticidal component can easily be replaced as a consumable at any time.

DETAILED DESCRIPTION OF THE PREFERRED EMBODIMENT

Embodiment 1

Figure 1:
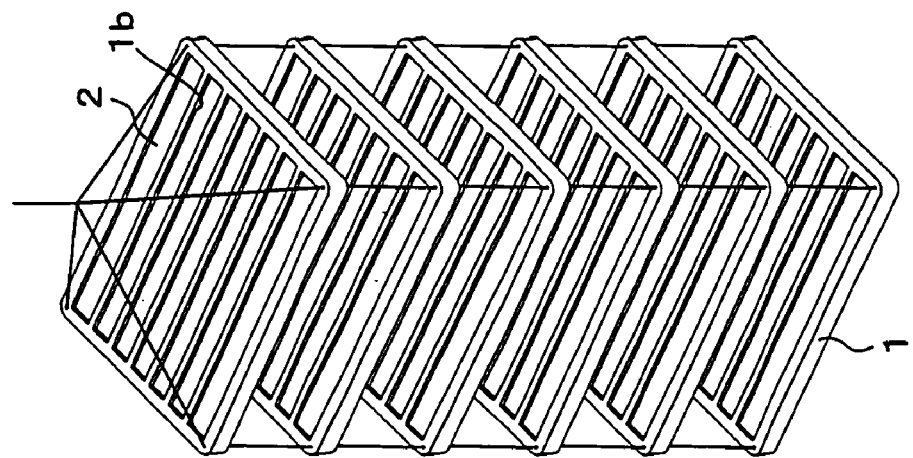
FIGS. 1(*a*), 1(*b*) and 1(*c*) show an example of the insect killer of the present invention, wherein FIG. 1(*a*) is a perspective view showing the structure of the insect killer, FIG. 1(*b*) is a right-side view thereof, and FIG. 1(*c*) is a perspective view showing the insect killer in which impregnated sheets are held in flat box-shaped holders.
Figure 1:
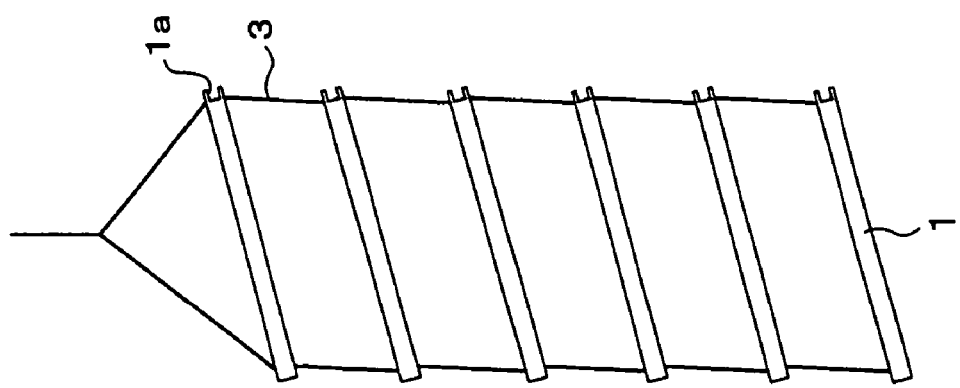
Figure 1:
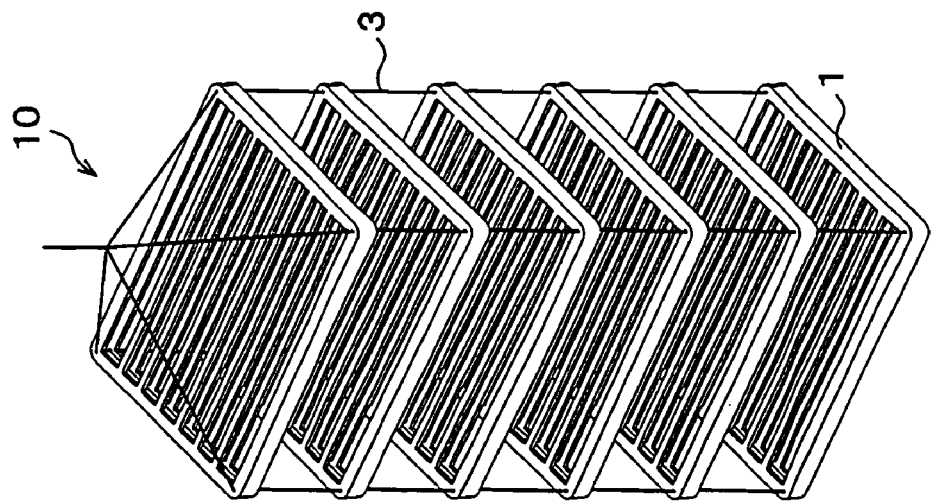

Referring to FIGS. 1(*a*) to 1(*c*), 2, 3(*a*) to 3(*e*), 4(*a*), and 4(*b*), an embodiment of the invention is described below.

Referring to FIGS. 1(*a*), 1(*b*) and 1(*c*), an insect killer as an embodiment of the invention has a completed structure or a working structure, which comprises sheets 2 impregnated with an insecticidal component which volatilizes at an ordinary temperature, flat box-shaped holders 1 (for example, six holders) (as the flat holder) for holding the sheets 2, and suspension cords 3, wherein the holders 1 are suspended by the cords 3.

Each suspension cord 3 serves as the support member for three-dimensionally assembling the plurality of the flat box-shaped holders 1. Specifically, the support member may be not only a cord such as the suspension cord 3 according to this embodiment but also a flexible linear member such as a string and a piano wire.

Figure 2:
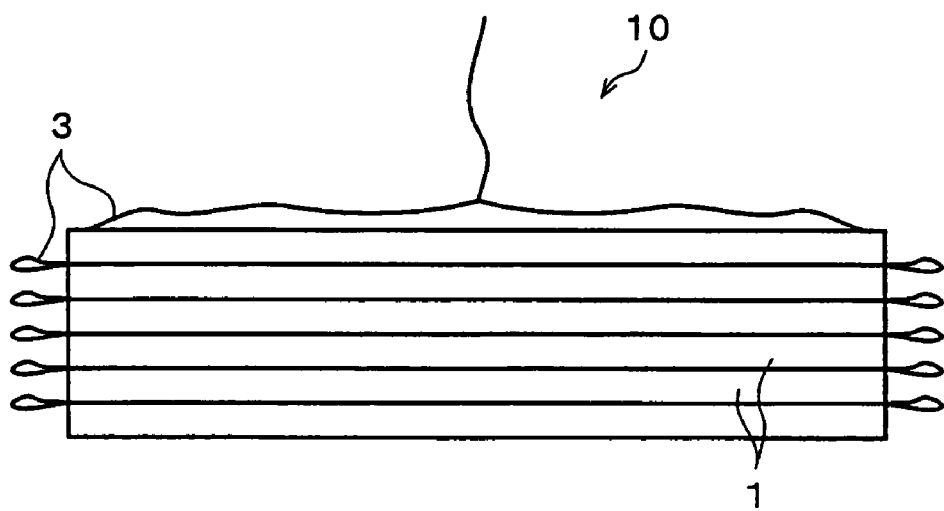
FIG. 2 is a front view showing a folded structure of the insect killer.
Figure 3:
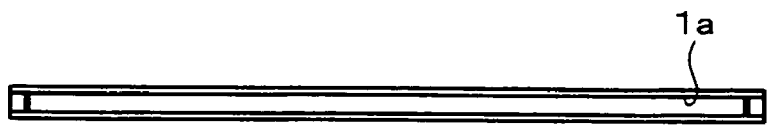
FIG. 3(*a*) is a plan view showing the structure of the flat box-shaped holder of the insect killer, FIG. 3(*b*) is a front view thereof, FIG. 3(*c*) is a bottom view thereof, FIG. 3(*d*) is a right-side view thereof, and FIG. 3(*e*) is a sectional view thereof.
Figure 3:
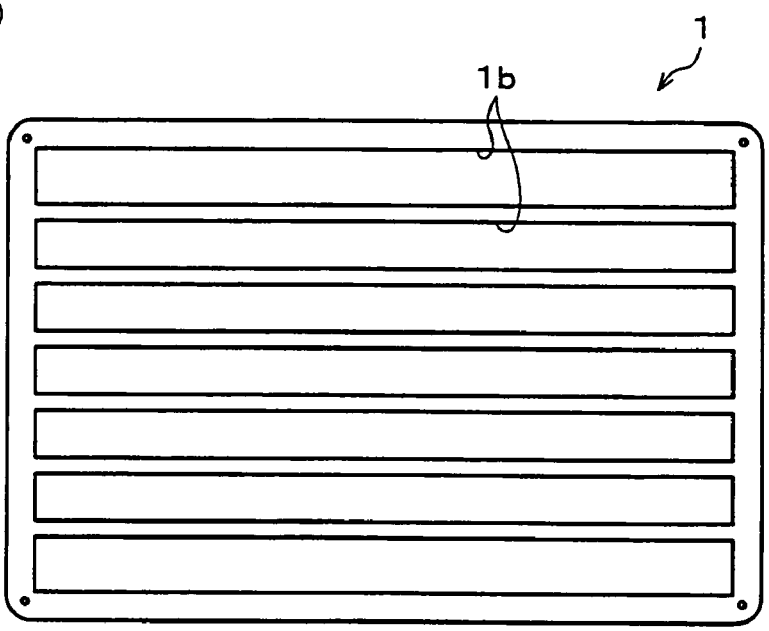
Figure 3:
Figure 3:
Figure 3:

The suspension cord 3 serving as the support member has flexibility. When not used, therefore, the insect killer 10 can readily be folded into a compact form as shown in FIG. 2.

For example, each sheet 2 is made of a paper sheet impregnated with the insecticidal component which volatilizes at an ordinary temperature. The impregnate content of the insecticidal component may be appropriately determined depending on the type of the insecticidal component for use, the volume of the room where the insect killer 10 will be used, the time period of use of the insect killer 10, and the like. For example, such an impregnate content is from 1 mg to 10 g per 1 m$^2$ of the transpiration surface of the sheet.

In this embodiment, for example, the insect killer 10 is suspended in a room of 6.6 to 16.6 m$^2$ (4 to 10 tatami mats) and used in killing a pest such as a mosquito. The use of the insect killer of the present invention is not limited to such a use, and for example, it may be suspended in a piece of furniture such as a chest and used to repel a clothes insect.

In the embodiment, for example, the insecticidal or insect-repellent component has a vapor pressure of at least $1 \times 10^{-6}$ mmHg at 25° C.

Examples of such an insecticidal or insect-repellent component include pyrethroid compounds such as
1-ethynyl-2-methyl-2-pentenyl 3-(2-chloro-2-fluorovinyl)-2,2-dimethylcyclopropane-1-carboxylate,
2,3,5,6-tetrafluoro-4-methylbenzyl 3-(2-methyl-1-propenyl)-2,2-dimethylcyclopropanecarboxylate,
2,3,5,6-tetrafluoro-4-methylbenzyl 3-(2-chloro-2-fluorovinyl)-2,2-dimethylcyclopropanecarboxylate,
2,3,5,6-tetrafluoro-4-methylbenzyl 3-(1-propenyl)-2,2-dimethylcyclopropanecarboxylate,
1-ethynyl-2-methyl-2-pentenyl(1R)-3-(2-methyl-1-propenyl)-2,2-dimethylcyclopropanecarboxylate (general name: empenthrin),
2,3,5,6-tetrafluorobenzyl(1R)-trans-3-(2,2-dichlorovinyl)-2, 2-dimethylcyclopropanecarboxylate (general name: trans-fluthrin),
2,3,5,6-tetrafluoro-4-methoxymethylbenzyl(1R)-trans-3-(1-propenyl (E/Z=about 8/1))-2,2-dimethylcyclopropanecarboxylate,
2,3,5,6-tetrafluoro-4-methoxymethylbenzyl(1R)-trans-3-(2-methyl-1-propenyl)-2,2-dimethylcyclopropanecarboxylate,
2,3,5,6-tetrafluoro-4-methylbenzyl(1R)-trans-3-(1-propenyl (E/Z=about 8/1))-2,2-dimethylcyclopropanecarboxylate;
2,2-dichlorovinyl dimethyl phosphate; N,N-diethyl-m-toluamide; and
carane-3,4-diol etc.

In this embodiment, paper is used for the sheet 2. However, any material may be used for the sheet 2, and examples of such a material include a synthetic resin sheet, aluminum, cotton cloth, hemp cloth, wool, felt, and non-woven fabric. A paper or aluminum sheet having a resin finish surface may also be used.

Examples of the resin for the sheet 2 include a polyolefin resin such as a homopolymer of α-olefin such as polyethylene,
an ethylene α-olefin copolymer such as an ethylene-propylene copolymer, an ethylene-butene-1 copolymer, an ethylene-4-methyl-1-pentene copolymer, and an ethylene-hexene copolymer, and a copolymer of ethylene and a derivative of an organic carboxylic acid having an ethylenic unsaturated bond, such as an ethylene-methyl methacrylate copolymer, an ethylene-vinyl acetate copolymer, an ethylene-acrylic acid copolymer, and an ethylene-vinyl acetate-methyl methacrylate copolymer; and polyvinyl alcohol, polyvinyl acetate, polycarbonate, polyester, polyamide, polystyrene, poly(methyl methacrylate), an acrylonitrile-butadien-styrene copolymer, and poly(vinyl chloride) etc.

Examples of an elastomer for the sheet include natural rubber, isoprene rubber, isobutylene-isoprene rubber (butyl rubber), butadiene rubber, styrene-butadiene rubber, ethylene-propylene rubber, nitrile rubber, silicone rubber, acrylic rubber, and fluoro rubber etc.

Examples of a thermoplastic elastomer for the sheet include a styrene type, a hydrogenated styrene type, an olefin type, a specific polyolefin type, a urethane type, an ester type, a polyamide type, an vinyl chloride type, a vinyl chloride/nitrile rubber type, and a vinyl chloride/urethane type etc.

Referring to FIGS. 3(a) to 3(e), the flat box-shaped holder 1 has a structure capable of holding the impregnated sheet 2 and a structure capable of facilitating volatilization of the insecticidal component from the impregnated sheet 2 held in the holder 1. Specifically, the flat box-shaped holder 1 is in the shape of a flat rectangular box so as to hold the rectangular sheet 2. The upper end of the flat box-shaped holder 1 has a sheet-receiving opening 1a for receiving the impregnated sheet 2. The front has sheet-exposing apertures 1b, which are provided for volatilizing the insecticidal component from the held sheet 2 and arranged in a grid pattern.

In this embodiment, the sheet-exposing apertures 1b are arranged in a grid pattern of horizontal stripes. However, the pattern is not limited to the grid of horizontal stripes, and for example, may be a grid of vertical stripes or a lattice. In addition, the pattern of the sheet-exposing apertures 1b is not limited to the grid or lattice, and a plurality of the apertures in any shape are sufficient. The area of the sheet-exposing apertures 1b may appropriately be changed depending on the type of the insecticidal component for use. For example, the ratio of the aperture area to the area of the impregnated sheet 2 is from 50% to 95%.

In this embodiment, the front of the flat box-shaped holder 1 has a rectangular shape. However, the shape of the front is not limited to a rectangle, and may be any other polygon such as a triangle and a pentagon, a circle, an ellipse, or any other form.

In this embodiment, a plurality of the flat box-shaped holders 1 are provided, for example, one of which has such a size that it can hold one of six equal parts of an A4 size sheet, as the impregnated sheet 2. In this embodiment, therefore, the insect killer 10 has six pieces of the flat box-shaped holders 1.

In the invention, the size is not limited to A4, and a sheet of any size such as a size of A3 to A5 may be divided into any parts to be held as the impregnated sheet 2.

Referring to FIG. 1(b) showing the right side, the insect killer 10 of this embodiment has six pieces of the flat box-shaped holders 1 arranged in parallel, wherein each holder 1 is inclined in such a manner that its front is placed lower than its back. The sheet-receiving opening 1a is located at the upper end. Such a configuration prevents each impregnated sheet 2 from slipping down from the sheet-receiving opening 1a of each flat box-shaped holder 1, when the insect killer 10 is suspended. In addition, the respective holders 1 are inclined and arranged in parallel, so that a wind in the horizontal direction of the insect killer 10 can facilitate the diffusion of the insecticidal component over the room.

In this embodiment, a plurality of through holes may be formed in the impregnated sheet 2. Such holes can effectively provide air ventilation characteristics for the impregnated sheet 2 and therefore can increase the efficiency of diffusion of the insecticidal component over the room.

Figure 4:
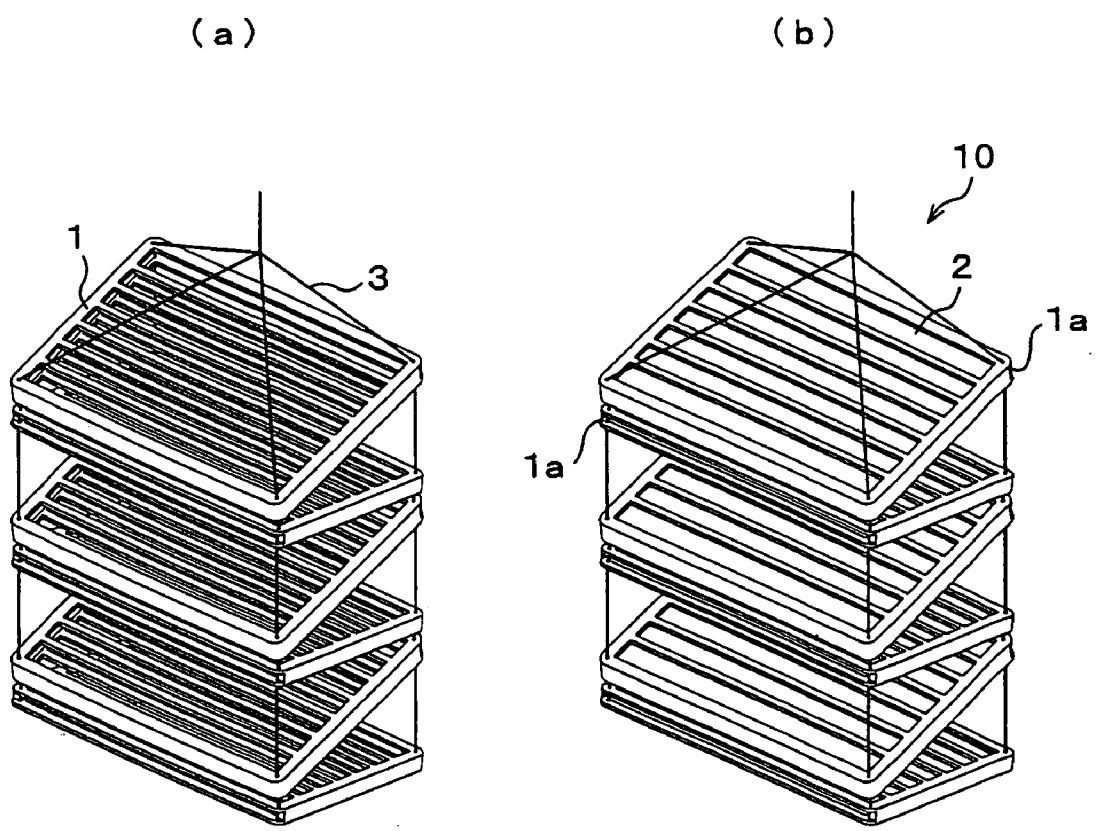
FIG. 4(*a*) is a perspective view showing another structure of the insect killer, and FIG. 4(*b*) is a perspective view showing the insect killer in which the impregnated sheets are held in flat box-shaped holders.

In this embodiment, six holders 1 are arranged in parallel and inclined in such a manner that each front side is located lower than each back side, as shown in FIGS. 1(a), 1(b) and 1(c). However, such an arrangement is not essential. For example, the holders 1 may be arranged and inclined in a zigzag pattern as shown in FIGS. 4(a) and 4(b). Such an arrangement can also facilitate the diffusion of the insecticidal component over the room, when a wind blows in the horizontal direction of the insect killer 10. In such a case, the sheet-receiving opening 1a should be located at the upper end of the flat box-shaped holder 1.

A description will be provided of how to use the insect killer 10 having the above-described structure.

On the market, the insect killer 10 is folded as shown in FIG. 2 into a compact form. For example, the insecticidal component-impregnated sheets 2 are also packed in a sealed bag (not shown).

When the insect killer 10 is converted from such a compact form to a working form, the impregnated sheets 2 are taken out of the bag and then each inserted from the sheet-receiving opening 1a into each flat box-shaped holder 1. The suspension cords 3 are then suspended from the ceiling of a room, the front of an air conditioner or the like, for the purpose of repelling a pest such as a mosquito and a fly.

In the above-described embodiment, the insecticidal component-impregnated sheets 2 on the market are packed in a sealed bag (not shown). However, such a form is not essential. In the manufacturing product, the insecticidal component-impregnated sheets 2 may originally be held in the flat box-shaped holders 1, respectively, and the whole structure of the insect killer 10 may be hermetically packed in such a state as shown in FIG. 2. Such a product has the merit that the user does not have to touch the impregnated sheets 2 directly.

In the insect killer 10 of this embodiment, each impregnated sheet 2 can be detachably or freely removably held in each flat box-shaped holder 1. Thus, the sheets 2 impregnated with the insecticidal component which volatilizes at an ordinary temperature can be held into the plurality of the flat box-shaped holders 1, respectively, which can then be three-dimensionally assembled on the suspension cords 3.

Each flat box-shaped holder 1 has the sheet-exposing apertures 1b for volatilizing the insecticidal component from the held sheet 2. Thus, the insect killer 10 having the three-dimensionally assembled holders 1 and being placed in a room can kill a pest such as a mosquito.

The insecticidal component is impregnated in each sheet 2 so that a wide area can be provided for volatilization of the insecticidal component. A plurality of the sheets can provide a further increased efficiency of diffusion of the insecticidal component.

Each sheet 2 impregnated with the insecticidal component which volatilizes at an ordinary temperature is held in each flat box-shaped holder 1. Thus, each impregnated sheet 2 can be prevented from being directly touched during use, and such a structure is hygienic.

In addition, the flat box-shaped holder 1 can reinforce the sheet 2.

The insect killer 10 provided according to the embodiment can have a slim and compact form during commercial sale or storage, can easily be assembled for use and can have a high efficiency of diffusion of the insecticidal component so that it can exert its effect in a relatively wide space such as a living room.

In the insect killer 10 of this embodiment, each suspension cord 3 is a flexible linear member for three-dimensionally suspending a plurality of the flat holders. Thus, the flat box-shaped holders 1 can be three-dimensionally suspended by the suspension cords 3, for example, from the ceiling of a room or the like.

Thus, the insect killer 10 of this embodiment can easily be set at an airy place so that the efficiency of diffusion of the insecticidal component can further be increased.

In the insect killer 10 of this embodiment, each impregnated sheet 2 may have through holes. Such holes can be effective at securing air ventilation for the sheet 2, so that the efficiency of diffusion of the insecticidal component can further be increased.

In the insect killer 10 of this embodiment, the size and number of the flat box-shaped holders 1 correspond to the size and number of the equal parts of the A4 size. More specifically, each flat box-shaped holder 1 has a size of about 8 cm long×about 12 cm wide, which corresponds to the size of one of six equal parts of the A4 size, and the number of the holders 1 is six.

Thus, the folded insect killer 10 is handy-sized and easily portable, while the assembled insect killer 10 can have an efficient size or area for the diffusion of the insecticidal component.

In the insect killer 10 of this embodiment, the sheet-receiving opening 1a is formed at an end portion of the flat box-shaped holder 1, and the insecticidal component-impregnated sheet 2 can be inserted from the sheet-receiving opening 1a into the holder 1.

Thus, the insecticidal component-impregnated sheet 2 can easily be replaced, and the sheet 2 running out of the insecticidal component can easily be replaced as consumable at any time.

Embodiment 2

Figure 5:
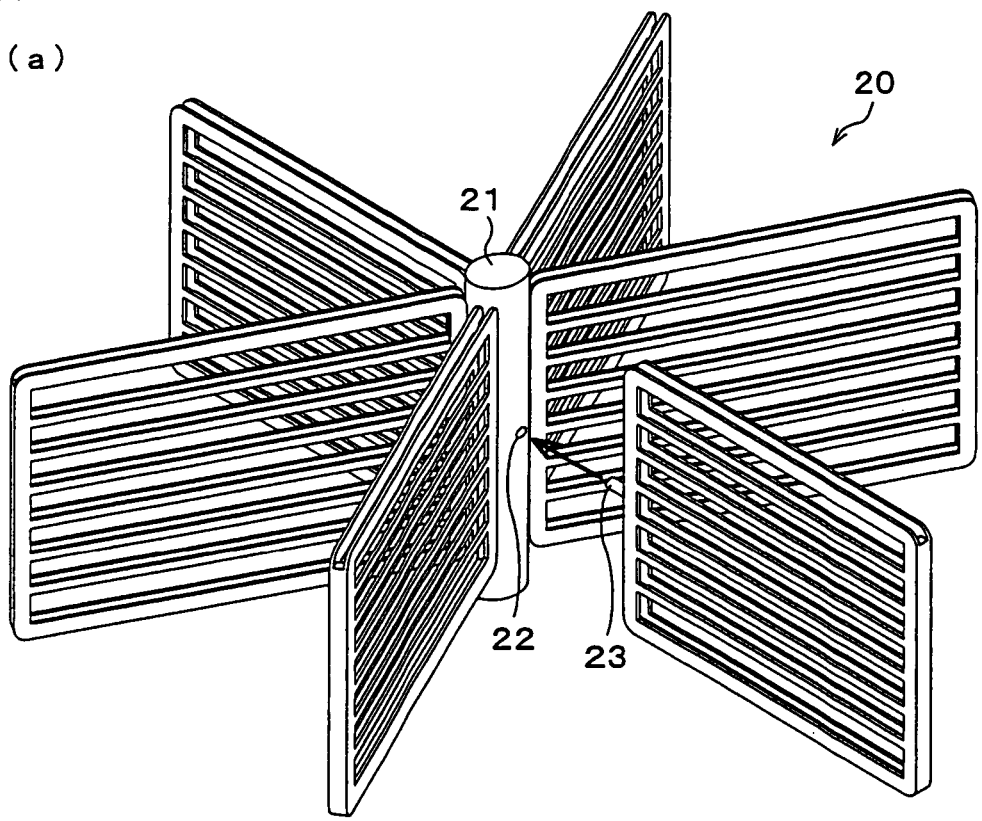
FIGS. 5(*a*) and 5(*b*) show another example of the insect killer of the present invention, wherein FIG. 5(*a*) is a perspective view showing the structure of the insect killer, and FIG. 5(*b*) is a perspective view showing the insect killer in which the impregnated sheets are held in flat box-shaped holders.
Figure 5:
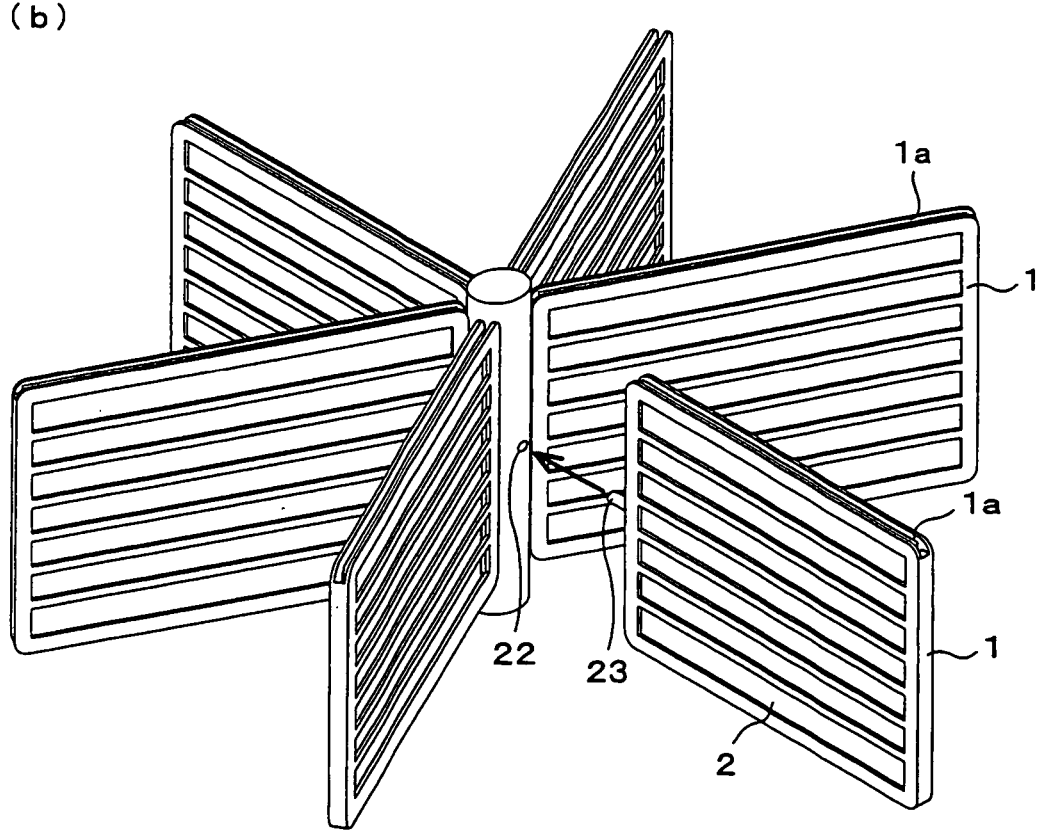
Figure 6:
FIG. 6(*a*) is a plan view showing the structure of the flat box-shaped holder of the insect killer, FIG. 6(*b*) is a front view thereof, FIG. 6(*c*) is a bottom view thereof, FIG. 6(*d*) is a left-side view thereof, and FIG. 6(*e*) is a right-side view thereof.
Figure 6:
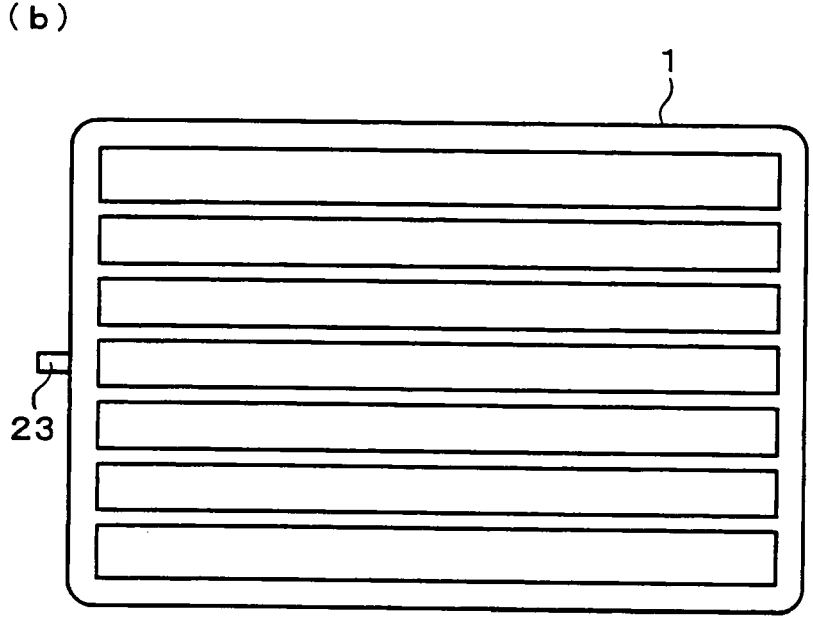
Figure 6:
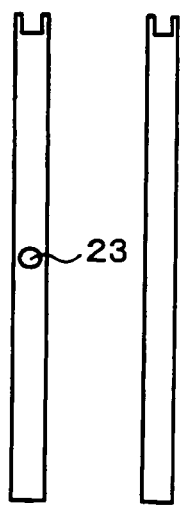
Figure 6:
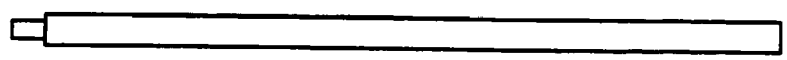

Referring to FIGS. 5 and 6, another embodiment of the invention is described below. This embodiment has the same elements as those in Embodiment 1, except for those described below. For convenience in description, therefore, an element having the same function as the element shown in the drawings for Embodiment 1 will be represented by the same reference numeral and will not further be described below.

Referring to FIGS. 5(a) and 5(b), an insect killer 20 of this embodiment, which differs from the suspension type insect killer 10 of Embodiment 1, comprises a core member 21 serving as the support member and the flat box-shaped holders 1 which are radially attached to the core member 21 in an upright position.

In this embodiment, the core member 21 has holes 22, and a side face of each flat box-shaped holder 1 has a single pin 23 as shown in FIGS. 6(a) to 6(e). In this embodiment, for example, the core member 21 may be a cylindrical resin product. However, the core member 21 is not limited to the cylinder, and may have any shape, as long as it can hold the plurality of the flat box-shaped holders 1 in a radially spreading pattern and can eventually be placed at the center between the holders 1.

The insect killer 20 having the above-described structure is assembled by attaching each flat box-shaped holder 1 to the core member 21, wherein the attachment is made by inserting the pin 23 of each holder 1 into each hole 22 of the core member 21.

In this embodiment, only a single piece of the pin 23 is formed in each flat box-shaped holder 1. However, such a structure is not essential. Two or more pins may be provided, and holes may be formed at the corresponding sites in the core member 21. In this embodiment, the pin 23 is provided, but such a pin is not essential for the invention. For example, the holder may be fixed onto the core member 21 by means of an adhesive double-coated tape. The insect killer 20 can also easily be assembled by such means.

In this embodiment, a single piece of the pin 23 is provided. Thus, each holder 1 attached to the core member 21 can be rotated about the pin 23 so that the tilt angle of each projecting holder 1 can be changed. In such a case where the insect killer 20 is suspended, therefore, the rotational speed of the insect killer 20 can be controlled to some extent and therefore the efficiency of diffusion of the insecticidal component can be regulated.

In this embodiment, the insect killer 20 is a direct storage type and does not rotate. However, such a structure is not essential. For example, a rotation drive unit (rotation drive means) (not shown) may be provided under the core member 21 and connected to the core member 21 so that the core member 21 can be driven and rotated around its axis. In such a structure, the flat box-shaped holders 1 can be rotated about the core member 21, which serves as a rotating shaft.

In this embodiment, the insect killer is a direct storage type as described above. Alternatively, a suspension cord 3 may be attached to the upper end of the core member 21 similarly to Embodiment 1, so that the insect killer can be suspended from the ceiling of a room or the like. In such a case, the efficiency of diffusion of the insecticidal component can be increased without the driving force.

In this embodiment as described above, the insect killer 20 as formed has the flat box-shaped holders 1, which radially project from the core member 21 serving as the support member.

For example, when the insect killer 20 is suspended, it can rotate about the core member 21 by wind blowing so that the efficiency of diffusion of the insecticidal component can further be increased.

In this embodiment, when the insert killer 20 is assembled, the pin 23 formed on the side face of the flat box-shaped holder 1 is inserted into the hole 22 of the core member 21. Thus, the insect killer 20 can easily be assembled, which comprises the flat box-shaped holders 1 radially attached to the core member 21.

The insect killer 20 provided according to this embodiment can have a slim and compact form during commercial sale or storage, can easily be assembled for use with reliability and can have a high efficiency of diffusion of the insecticidal component so that it can exert its effect in a relatively wide space such as a living room.

In the insect killer 20 of this embodiment, each flat box-shaped holder 1 is rotatable about a single piece of the pin 23. Thus, the angle of each flat box-shaped holder 1 attached to the core member 21 is easily changeable. For example, therefore, in the suspended insect killer 20 comprising the flat box-shaped holders 1 radially attached in an upright position, the attachment angle of each holder 1 can be effective at controlling the rotational speed of the insect killer 20, and therefore the efficiency of diffusion of the insecticidal component can be regulated.

In the insect killer 20 of this embodiment, a drive unit (not shown) may be connected to the core member 21 so as to drive and rotate the core member 21. In such a case, the flat box-shaped holders 1 radially attached to the core member 21 can be rotated by its driving force about the core member 21, which serves as the rotating shaft. Thus, the efficiency of diffusion of the insecticidal component can be increased without wind blowing.

Embodiment 3

Referring to FIGS. 7 to 12, yet another embodiment of the invention is described below. This embodiment has the same elements as those in Embodiment 1, except for those described below. For convenience in description, therefore, an element having the same function as the element shown in the drawings for Embodiment 1 will be represented by the same reference numeral and will not further be described below.

According to Embodiment 1, the flat box-shaped holders 1 are inclined and arranged in parallel in one type of the insect killer 10 or are inclined and arranged in a zigzag pattern in another type of the insect killer 10. In the insect killer 20 of Embodiment 2, the flat box-shaped holders 1 spread radially.

However, such an arrangement is not essential for the insect killer of the present invention. The flat box-shaped holders 1 each having the same shape may be three-dimensionally arranged in any pattern.

Figure 7:
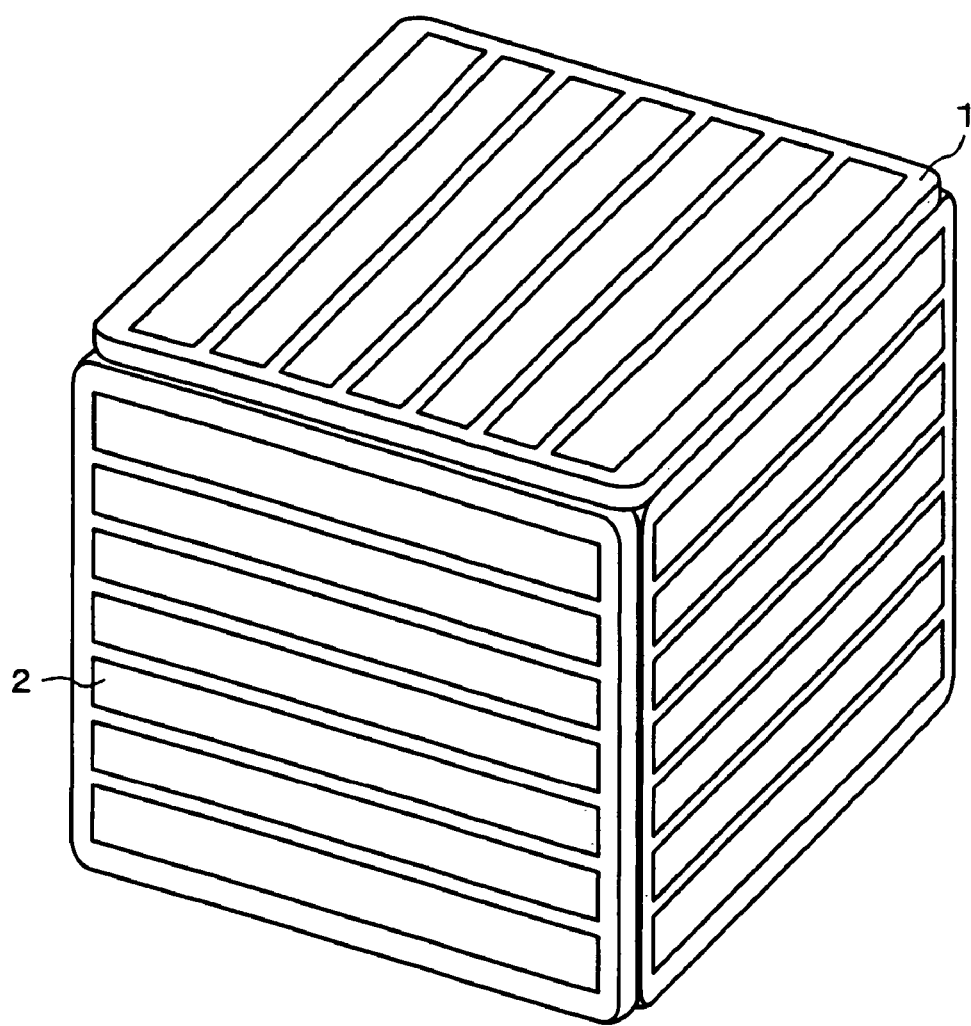
FIG. 7 is a perspective view showing yet another example of the insect killer of the present invention, which has a hexahedron structure.

Referring to FIG. 7, for example, six flat box-shaped holders 1 may be assembled into a cube (hexahedron).

In such a case, a pin (or pins) (not shown), which serves as the support member, is formed on each flat box-shaped holder 1 so that the respective flat box-shaped holders 1 can be fixed in the form of the cube.

According to such a structure, the respective holders can be disassembled and piled for market, while the user can easily assemble the holders 1 into the cube.

Figure 8:
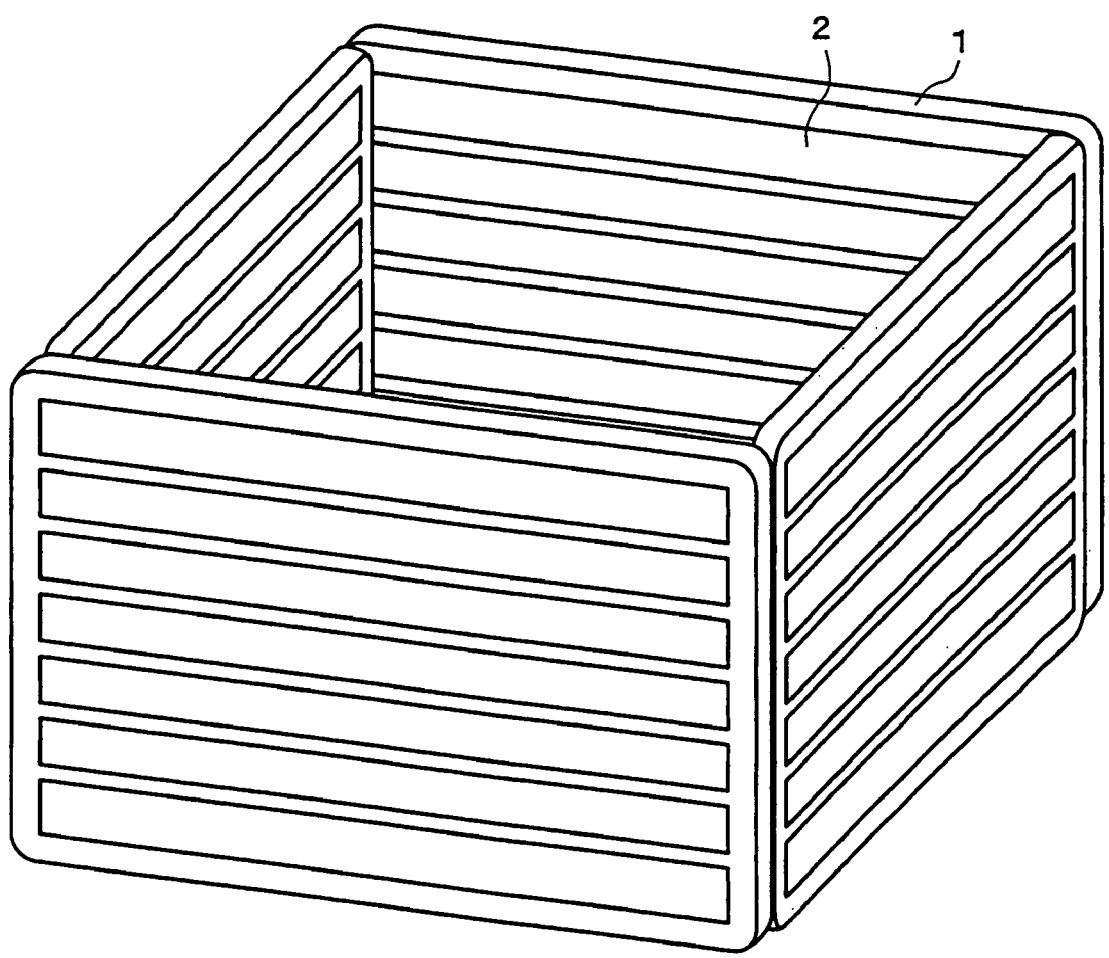
FIG. 8 is a perspective view showing a modification of the insect killer structure, which is in the shape of a box or tube having a rectangular horizontal face.
Figure 9:
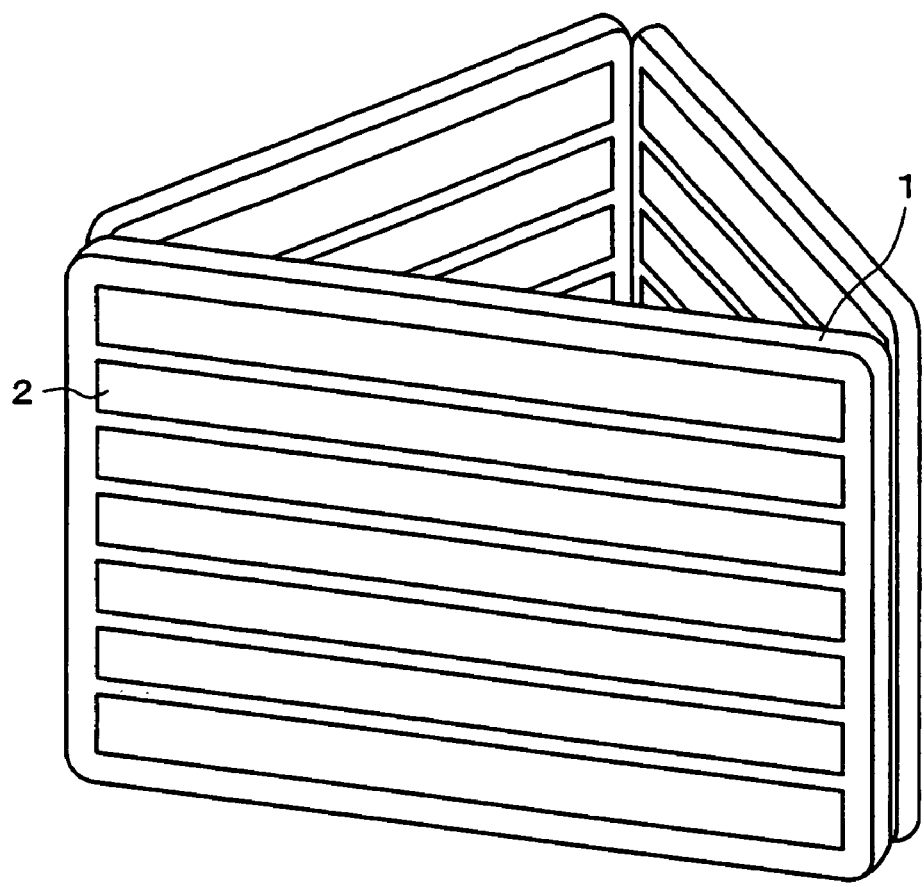
FIG. 9 is a perspective view showing another modification of the insect killer structure, which is in the shape of a box or tube having a triangular horizontal face.
Figure 10:
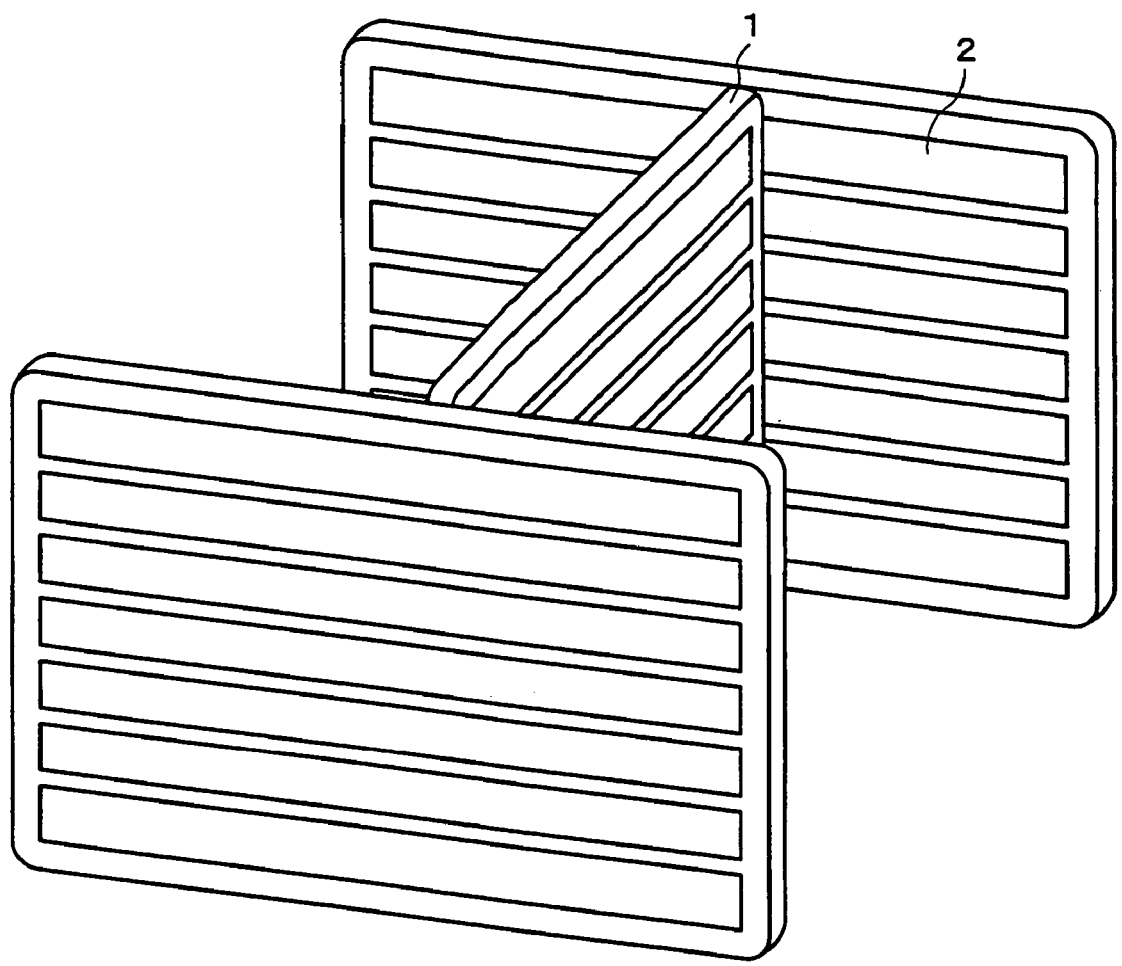
FIG. 10 is a perspective view showing yet another modification of the insect killer structure, which has an H-shaped horizontal face.
Figure 11:
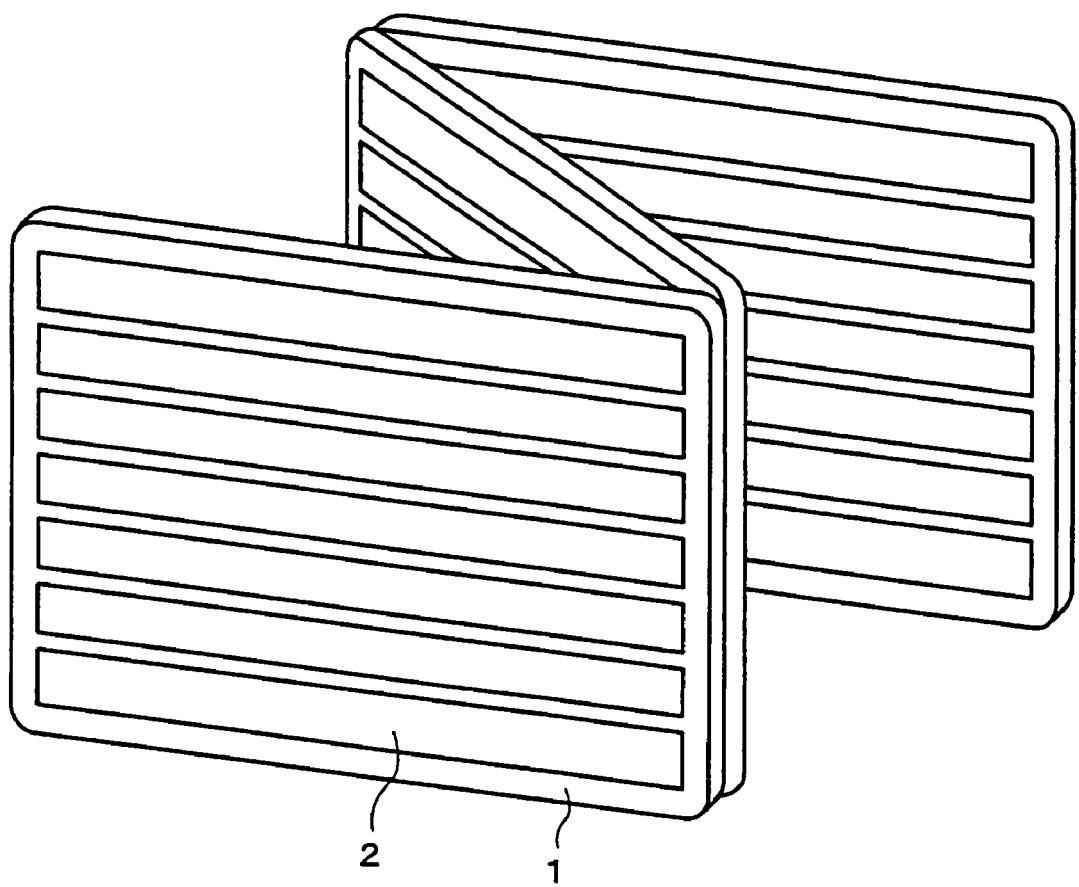
FIG. 11 is a perspective view showing still another modification of the insect killer structure, which has a folding-screen shape.

According to such a technique, the holders may be assembled into any other form such as a box having an upper opening and a horizontal face of a rectangle or a rhombus as shown in FIG. 8 and a box having an upper opening and a horizontal face of a triangle as shown in FIG. 9. The horizontal face may be any other polygon. In the case of FIG. 8 or 9, the holders may form a tube in which the lower side also has an opening. The horizontal face is not limited to the polygon. For example, the holders may be assembled into a box having an H-shaped horizontal face as shown in FIG. 10 or into a folding-screen form as shown in FIG. 11.

Figure 12:
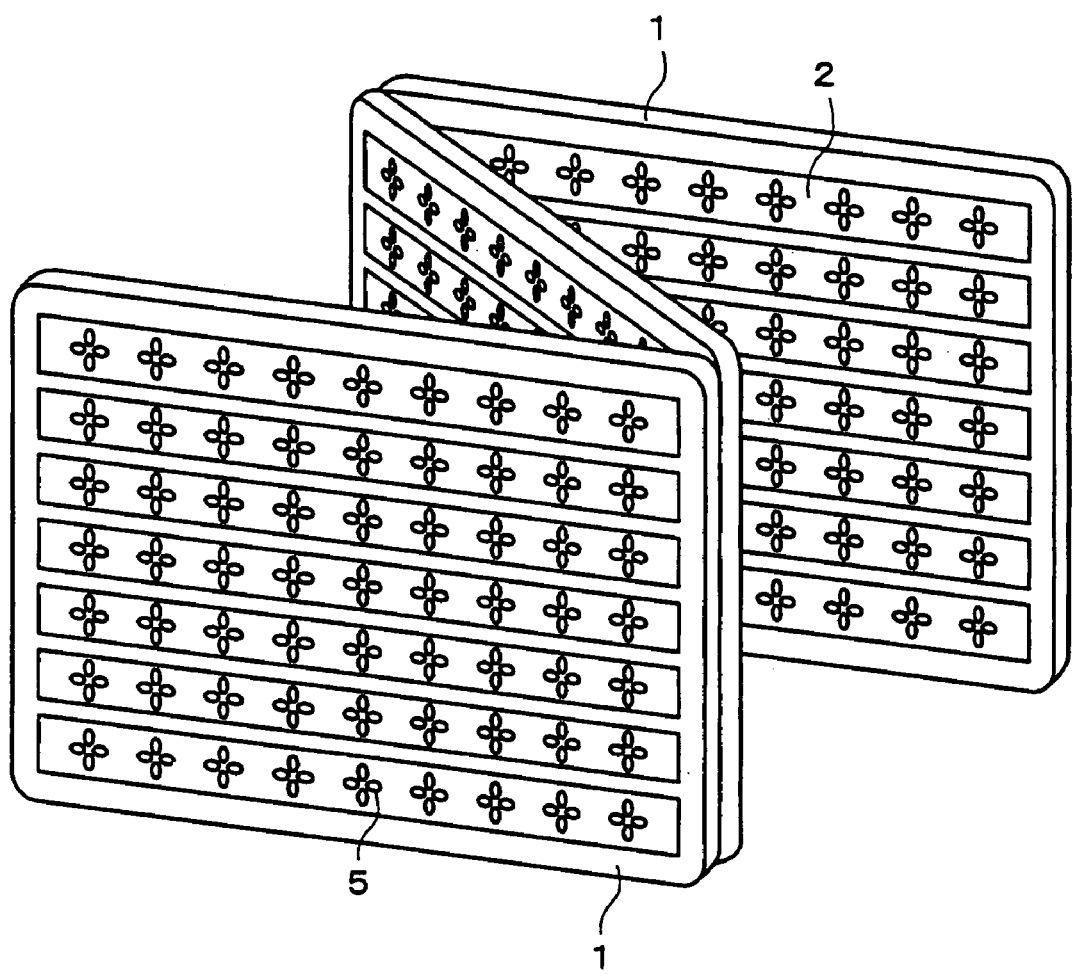
FIG. 12 is a perspective view showing an insect killer in which each impregnated sheet has a plurality of holes.
Figure 13:
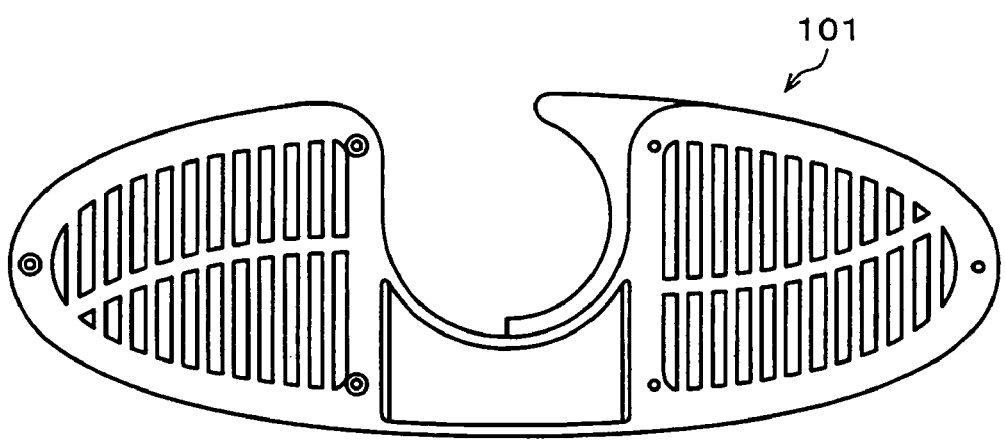
FIGS. 13(*a*) and 13(*b*) show the structure of a conventional insect killer, wherein FIG. 13(*a*) is a front view of the male part, and FIG. 13(*b*) is a front view of the female part.
Figure 13:
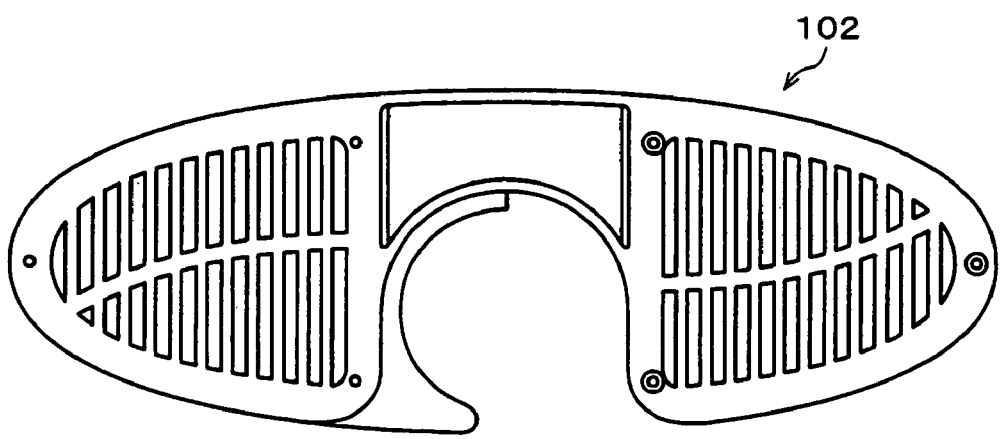
Figure 14:
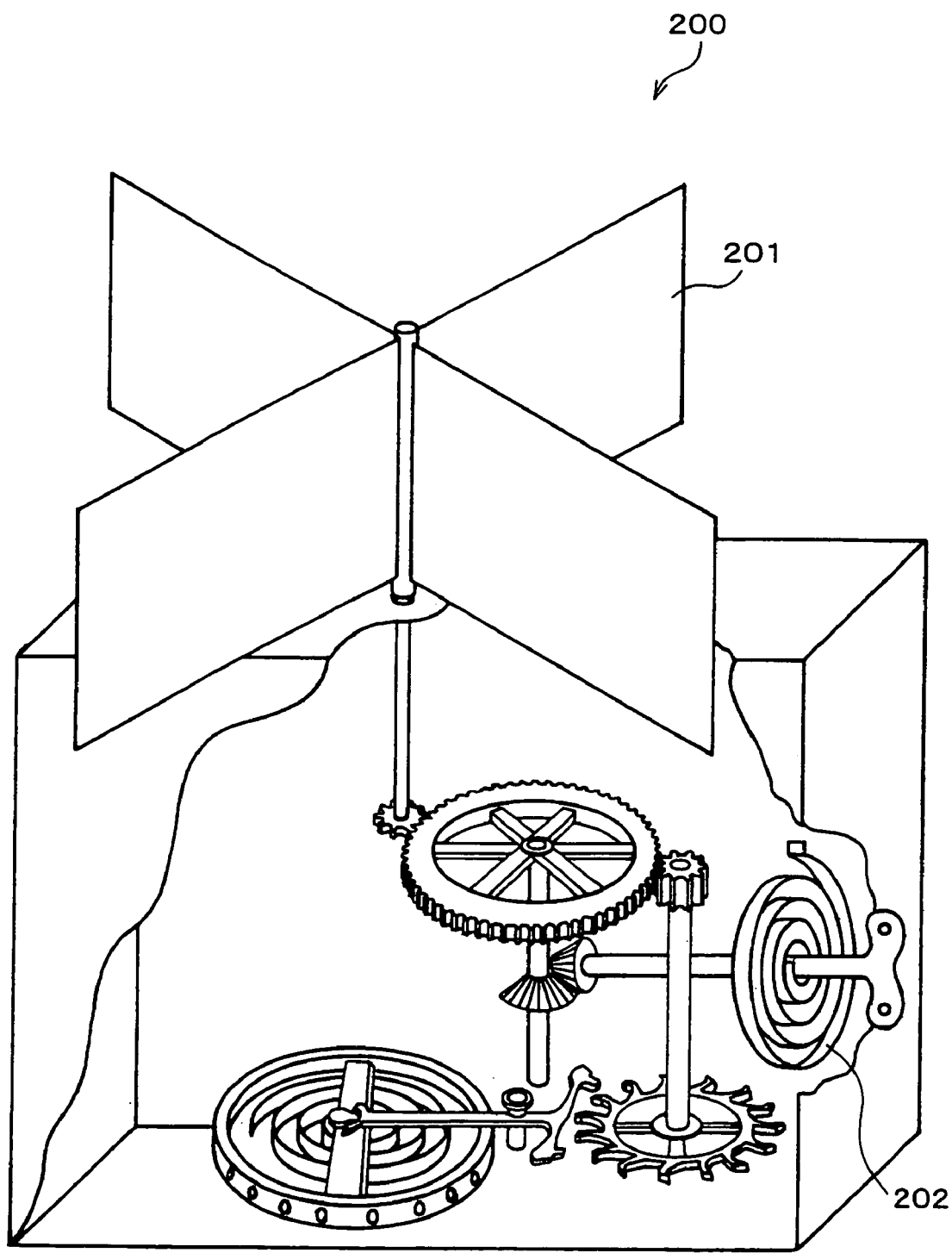
FIG. 14 is a cutaway perspective view showing the structure of another conventional insect-repellent device.

In each of such forms, each impregnated sheet 2 may have a plurality of holes 4 as shown in FIG. 12. The holes 4 may be arranged in a mesh pattern or may be in a variety of shapes or patterns in aesthetic terms. While the configuration of the holes 4 is described with respect to Embodiment 1, such holes may also be formed in the impregnated sheet 2 as described in Embodiment 2.

As an extension of such a design, for example, a lighting fixture may be placed inside the rectangular parallelepiped to form a lamp, so that the insect killer can serve as an interior decoration. Concerning the insect killer, therefore, the user can forget what it is.

The above-described embodiments are not intended to limit the scope of the present invention. A variety of modifications are possible within the scope of the claims appended hereto, and any appropriate combinations of the technical means or elements described in the different embodiments, respectively, may also be included in the technical scope of the present invention.

As described above, the insect killer of the present invention comprises: a sheet impregnated with an insecticidal component which volatilizes at an ordinary temperature; a flat holder for detachably holding the sheet, the flat holder having a sheet-exposing aperture for volatilizing the insecticidal component from the sheet; and a support member for three-dimensionally assembling a plurality of the flat holders.

Thus, the sheets each impregnated with the insecticidal component which volatilizes at an ordinary temperature can be held in the flat holders, respectively, which can three-dimensionally be assembled with or on the support member.

The flat holder has the sheet-exposing aperture. Thus, the insect killer having the three-dimensionally assembled flat holders can be placed in a room to kill a pest such as a mosquito.

The insecticidal component is impregnated in the sheet so that a wide area can be provided for volatilization of the insecticidal component. A plurality of the sheets can provide a further increased efficiency of diffusion of the insecticidal component.

The sheet impregnated with the insecticidal component which volatilizes at an ordinary temperature is held in the flat holder. Thus, the sheet can be prevented from being directly touched during use, and such a structure is hygienic. In addition, the flat holder can reinforce the sheet.

Thus, the provided insect killer can have a slim and compact form during commercial sale or storage, can easily be assembled for use and can have a high efficiency of diffusion of the insecticidal component so that it can exert its effect in a relatively wide space such as a living room.

In the above insect killer, the support member may comprise a flexible linear member for three-dimensionally suspending a plurality of the flat holders.

For example, therefore, the plurality of the flat holders may be suspended from the ceiling of a room or the like by the flexible linear member. Thus, the insect killer of the present invention can easily be set at an airy place so that the efficiency of diffusion of the insecticidal component can further be increased.

In the above insect killer, the support member may comprise a core member placed at a center between the plurality of the flat holders to radially arrange the flat holders in an upright position.

Thus, the flat holders can be radially provided in an upright position around the core member, which serves as the support member, to form the insect killer.

For example, when the insect killer is suspended, it can rotate about the core member by wind blowing so that the efficiency of diffusion of the insecticidal component can further be increased.

In the insect killer of the present invention, the core member may have a hole, and the flat holder may have a side face provided with a pin, which can be inserted into the hole of the core member to allow the flat holder to be attached to the core member.

Thus, the pin formed on the side face of the flat holder is inserted into the hole of the core member, so that an insect killer can easily be assembled, which comprises the flat holders radially attached to the core member.

Thus, the provided insect killer can have a slim and compact form during commercial sale or storage, can easily be assembled for use with reliability and can have a high efficiency of diffusion of the insecticidal component so that it can exert its effect in a relatively wide space such as a living room.

In the above insect killer, the flat holder may have a single piece of the pin, and the flat holder may be attached so as to be rotatable about the pin.

In such a structure, the flat holder is rotatable about the single pin, so that the angle of the flat holder attached to the core member is easily changeable. For example, therefore, in a suspended insect killer comprising the flat holders radially attached in an upright position, the attachment angle of each flat holder can be changed so that the rotational speed of the insect killer can be controlled to some extent and therefore the efficiency of diffusion of the insecticidal component can be regulated.

In the above insect killer, the core member may be drivable and rotatable.

In such a structure, the flat holders radially attached to the core member can be rotated by its driving force around the core member, which serves as a rotating shaft. Thus, the efficiency of diffusion of the insecticidal component can be increased without wind blowing.

In the above insect killer, the sheet may have a plurality of holes.

In such a structure, the holes of the sheet can be effective at securing ventilation, so that the efficiency of diffusion of the insecticidal component can further be increased.

In the above insect killer, the flat holder may be a flat box having an end portion provided with a sheet-receiving opening for receiving the sheet.

In such a structure, the sheet impregnated with insecticidal component can be inserted from the sheet-receiving opening, which is formed at an end portion of the flat box as the flat holder, into the flat box.

In such a structure, the sheet impregnated with insecticidal component can easily be replaced. Thus, the sheet running out of the insecticidal component can easily be replaced as a consumable at any time.

What is claimed is:

1. A device for dispensing a volatile insecticide or repellent for volatilizing an insecticidal or insect-repellent component, comprising:
    a plurality of sheets, each sheet being impregnated with an insecticidal or insect-repellent component which can volatilize at a temperature of 25° C., each sheet having a plurality of holes;
    a plurality of flat holders for detachably holding the sheets, respectively, each flat holder having a sheet-exposing aperture for volatilizing the insecticidal or insect-repellent component from a respective held sheet, each flat holder comprising a flat box having an end portion provided with a sheet-receiving opening through which the respective sheet is insertable into and removable from the flat box; and
    a support member for three-dimensionally assembling the plurality of flat holders, the support member comprising a core member centrally arranged between the flat holders so as to radially arrange the flat holders in an upright position, the core member being drivable and rotatable.

2. A device according to claim 1, wherein the sheet-exposing aperture of each flat holder is arranged on a first surface of the flat holder, and wherein the sheet-receiving opening of each flat holder is arranged on an end surface of the flat holder, the end surface being perpendicular to the first surface.

* * * * *